(12) United States Patent
Benson et al.

(10) Patent No.: US 9,422,371 B2
(45) Date of Patent: *Aug. 23, 2016

(54) SURFACE-BOUND FLUORINATED ESTERS FOR AMINE CAPTURE

(71) Applicant: 3M INNOVATIVE PROPERTIES COMPANY, St. Paul, MN (US)

(72) Inventors: Karl E. Benson, St. Paul, MN (US); Charles M. Leir, Ironton, MN (US); George G. I. Moore, Afton, MN (US); Rahul R. Shah, Woodbury, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/531,556

(22) Filed: Nov. 3, 2014

(65) Prior Publication Data

US 2015/0057438 A1 Feb. 26, 2015

Related U.S. Application Data

(62) Division of application No. 11/856,140, filed on Sep. 17, 2007, now Pat. No. 8,906,703.

(60) Provisional application No. 60/871,256, filed on Dec. 21, 2006.

(51) Int. Cl.

| C07K 17/14 | (2006.01) |
|---|---|
| C07C 323/52 | (2006.01) |
| C07H 21/02 | (2006.01) |
| C07H 21/04 | (2006.01) |
| C07K 1/107 | (2006.01) |
| C07K 17/06 | (2006.01) |
| G01N 33/543 | (2006.01) |

(52) U.S. Cl.
CPC ............ *C07K 17/14* (2013.01); *C07C 323/52* (2013.01); *C07H 21/02* (2013.01); *C07H 21/04* (2013.01); *C07K 1/1077* (2013.01); *C07K 17/06* (2013.01); *G01N 33/54353* (2013.01)

(58) Field of Classification Search
CPC ............ G01N 33/54353; C07K 17/06; C07K 17/14; C07K 1/10; C07K 1/1077; C07C 19/08; C07C 21/18; C07C 21/185; C07C 49/167
See application file for complete search history.

(56) References Cited

U.S. PATENT DOCUMENTS

| 2,862,893 A | 12/1958 | Hwa |
|---|---|---|
| 3,719,698 A | 3/1973 | Tesoro |
| 4,035,316 A | 7/1977 | Yen |
| 4,837,289 A | 6/1989 | Mueller |
| 5,380,784 A | 1/1995 | Usuki |
| 5,494,961 A | 2/1996 | Lavoie |
| 5,494,975 A | 2/1996 | Lavoie |
| 5,525,662 A | 6/1996 | Lavoie |
| 5,548,024 A | 8/1996 | Lavoie |
| 5,616,764 A | 4/1997 | Lavoie |
| 5,627,259 A | 5/1997 | Thaler |
| 6,513,897 B2 | 2/2003 | Tokie |
| 6,696,157 B1 | 2/2004 | David |
| 6,765,036 B2 | 7/2004 | Dede |
| 6,883,908 B2 | 4/2005 | Young |
| 6,897,164 B2 | 5/2005 | Baude |
| 6,897,262 B2 | 5/2005 | Pears |
| 7,544,754 B2 | 6/2009 | Leir |
| 7,632,903 B2 | 12/2009 | Leir |
| 8,357,540 B2 | 1/2013 | Moore |
| 2005/0070627 A1 | 3/2005 | Falsafi |
| 2005/0106709 A1 | 5/2005 | Benson |
| 2005/0113477 A1 | 5/2005 | Oxman |
| 2008/0227169 A1 | 9/2008 | Benson |

FOREIGN PATENT DOCUMENTS

| EP | 0816310 | 1/1998 |
|---|---|---|
| EP | 0818431 | 1/1998 |
| JP | 63278913 | 11/1988 |
| WO | WO 2005/066121 | 7/2005 |

OTHER PUBLICATIONS

Albericio, "A New Strategy for Solid-Phase Depsipeptide Synthesis Using Recoverable Building Blocks", Organic Letters, Feb. 17, 2005, vol. 7, No. 4, pp. 597-600.

Fryxell, "Nucleophilic Displacements in Mixed Self-assembled Monolayers", Langmuir, 1996, vol. 12, No. 21, pp. 5064-5075.

Margel, "Peptide, protein, and cellular interactions with self-assembled monolayer model surfaces", Journal of Biomedical Materials Research, 1993, vol. 27, pp. 1463-1476.

Pittman, "Polymers Derived from Fluoroketones. I. Preparation of Fluoroalkyl Acrylates and Methacrylates", Journal of Polymer Science: Part A-1, Oct. 1966, vol. 4, No. 10, pp. 2637-2647.

Pittman, "Polymers Derived from Fluoroketones. III. Monomer Synthesis, Polymerization, and Wetting Properties of Poly (allyl Ether) and Poly (vinyl Ether)", Journal of Polymer Science: Part A-1, Jun. 1968, vol. 6, No. 6, pp. 1741-1750.

*Primary Examiner* — Shafiqul Haq
(74) *Attorney, Agent, or Firm* — Jean A. Lown

(57) ABSTRACT

A method for immobilizing an amino-containing material to a substrate is described. The method involves providing a tethering compound with two reactive groups: a substrate reactive group and a fluoroalkoxycarbonyl group. The method further involves preparing a substrate-attached tethering group by reacting the substrate reactive group of the tethering compound with a complementary functional group on the surface of a substrate. The substrate-attached tethering group has a fluoroalkoxycarbonyl group that can be reacted with an amino-containing material to form an immobilization group that connects the amino-containing material to the substrate.

5 Claims, No Drawings

SURFACE-BOUND FLUORINATED ESTERS FOR AMINE CAPTURE

CROSS REFERENCE TO RELATED APPLICATIONS

This application is a Divisional application of prior U.S. application Ser. No. 11/856,140, filed Sep. 17, 2007, now allowed, which claims benefit of U.S. Provisional Application No. 60/871,256 filed on Dec. 21, 2006, the disclosures of which are incorporated herein by reference in their entireties.

TECHNICAL FIELD

Methods for immobilizing amino-containing materials on a substrate are described.

BACKGROUND

Amino-containing materials such as amino-containing analytes, amino acids, DNA, RNA, proteins, cells, tissue, organelles, immunoglobins, or fragments thereof immobilized on a surface of a substrate can be used in numerous applications. For example, immobilized biological amino-containing materials can be used for the medical diagnosis of a disease or genetic defect, for biological separations, or for detection of various biomolecules. Immobilization of the amino-containing material is typically accomplished by reaction of the amino group with a reactive functional group that is covalently attached to the surface of the substrate.

Substrates having amino-reactive functional groups can be prepared by coating a substrate with a solution of a polymeric material that contains amino-reactive functional groups. Alternatively, substrates having amino-reactive functional groups can be prepared by coating a substrate with a solution of monomers that contain amine reactive functional groups followed by polymerization of the monomers. Exemplary amino-reactive monomers include, for example, N—[(meth)acryloxy]succinimide and vinyl azlactone. An amino-containing material can react with the N-acyloxysuccinimide group resulting in displacement of N-hydroxysuccinimide and formation of a carboxamide. An amino-containing material can react with the cyclic azlactone resulting in an opening of the ring structure.

Although polymeric surfaces that include a reactive functional group such as an N-acyloxysuccinimide group or an azlactone group can react readily with primary or secondary amino-containing materials, such reactive functional groups can suffer from a number of disadvantages. For example, many of the reactions with biological amino-containing materials are conducted in dilute aqueous solutions. Under these conditions, the N— acyloxysuccinimide functional group is known to undergo rapid hydrolysis. This competing reaction can cause incomplete or inefficient immobilization of the amino-containing materials on the substrate.

While azlactone functional groups are more stable to hydrolysis, it is difficult to synthesize an azlactone linked to any polymerizable group other than a vinyl group. The resulting polymeric material has amino-reactive functional groups directly attached to the polymer backbone. In some applications, this can make it difficult for the amino-containing material to get close enough to the amine reactive group for efficient immobilization.

SUMMARY OF THE INVENTION

A method of immobilizing an amino-containing material on a substrate and an article containing an immobilized amino-containing material are provided. More specifically, a tethering compound with two reactive groups is used to form an immobilization group that connects the amino-containing material to the substrate. A first reactive group of the tethering compound is capable of reacting with a complementary group on the substrate and a second reactive group is capable of reacting with a primary or secondary amino-containing material.

The method of immobilizing an amino-containing material on a substrate includes selecting a tethering compound of Formula I.

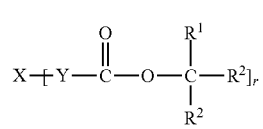

I

In Formula I, X is a substrate-reactive functional group selected from a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, disulfide, alkyl disulfide, benzotriazolyl, phosphono, phosphoroamido, phosphato, or ethylenically unsaturated group. Group Y is a single bond or a divalent group that includes an alkylene, heteroalkylene, arylene, or combination thereof. Optionally, when Y is a divalent group, Y can further include a carbonyl, carbonyloxy, carbonylimino, oxy, —NR$^3$— or combination thereof. Group R$^1$ is selected from hydrogen, fluoro, alkyl, or lower fluoroalkyl and each group R$^2$ is a lower fluoroalkyl. Group R$^3$ is selected from hydrogen, alkyl, aryl, or aralkyl. The variable r is equal to 1 when X is a monovalent group or equal to 2 when X is a divalent group. The tethering compounds of Formula I can be unsubstituted or substituted with a halo, alkyl, alkoxy, or combination thereof. The method of immobilizing an amino-containing material further includes providing a substrate having a complementary functional group capable of reacting with group X of the tethering compound and preparing a substrate-attached tethering group by reacting group X with the complementary functional group on the substrate to form an ionic bond, covalent bond, or combination thereof. The method still further involves reacting an amino-containing material with a fluoroalkoxycarbonyl group of the substrate-attached tethering group to form an immobilization group that connects the amino-containing material to the substrate.

In another aspect, an article is provided. The article includes a substrate with (a) an attached tethering group of Formula IV

that contains a fluoroalkoxycarbonyl group and (b) an attached immobilization group of Formula V.

The group U in Formulas IV and V is equal to the reaction product of a substrate-reactive functional group X and a complementary group G on the surface of the substrate. The substrate-reactive functional group X is selected from a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, disulfide, alkyl disulfide, benzotriazolyl, phosphono, phosphoroamido, phosphato, or ethylenically unsaturated group. Group Y in Formulas IV and V is a single bond or a divalent group that includes an alkylene, heteroalkylene, arylene, or combination thereof. Optionally, when Y is a divalent group, Y can further include a carbonyl, carbonyloxy, carbonylimino, oxy, —NR³— or combination thereof. In Formula IV, group R¹ is selected from hydrogen, fluoro, alkyl, or lower fluoroalkyl and each group R² is a lower fluoroalkyl. Group R³ is selected from hydrogen, alkyl, aryl, or aralkyl. Group T in Formula V is equal to the remainder of a primary or secondary amino-containing material of formula T-NHR⁴ absent the amino group of formula —NHR⁴. Group R⁴ is selected from hydrogen, alkyl, or a portion of a ring structure connected to group T.

The terms "a", "an", and "the" are used interchangeably with "at least one" to mean one or more of the elements being described.

The term "acyl" refers to a monovalent group of formula —(CO)R where R is an alkyl group and where (CO) used herein indicates that the carbon is attached to the oxygen with a double bond.

The term "acyloxy" refers to a monovalent group of formula —O(CO)R where R is an alkyl group.

The term "acyloxysilyl" refers to a monovalent group having an acyloxy group attached to a Si (i.e., Si—O(CO)R where R is an alkyl). For example, an acyloxysilyl can have a formula —Si[O(CO)R]$_{3-n}$L$_n$ where n is an integer of 0 to 2 and L is a halogen or acyloxy. Specific examples include —Si[O(CO)CH$_3$]$_3$, —Si[O(CO)CH$_3$]$_2$Cl, or —Si[O(CO)CH$_3$]Cl$_2$.

The term "alkoxy" refers to a monovalent group of formula —OR where R is an alkyl group.

The term "alkoxycarbonyl" refers to a monovalent group of formula —(CO)OR where R is an alkyl group.

The term "alkoxysilyl" refers to a monovalent group having an alkoxy group attached to a Si (i.e., Si—OR where R is an alkyl). For example, an alkoxysilyl can have a formula —Si(OR)$_{3-n}$(L$^a$)$_n$ where n is an integer of 0 to 2 and L$^a$ is a halogen or acyloxy. Specific examples include —Si(OCH$_3$)$_3$, —Si(OCH$_3$)$_2$Cl, or —Si(OCH$_3$)Cl$_2$.

The term "alkyl" refers to a monovalent group that is a radical of an alkane and includes groups that are linear, branched, cyclic, or combination thereof. The alkyl group typically has 1 to 30 carbon atoms. In some embodiments, the alkyl group contains 1 to 20 carbon atoms, 1 to 10 carbon atoms, 1 to 6 carbon atoms, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

The term "alkyl disulfide" refers to a monovalent group of formula —SSR where R is an alkyl group.

The term "alkylene" refers to a divalent group that is a radical of an alkane. The alkylene can be straight-chained, branched, cyclic, or combination thereof. The alkylene typically has 1 to 200 carbon atoms. In some embodiments, the alkylene contains 1 to 100, 1 to 80, 1 to 50, 1 to 30, 1 to 20, 1 to 10, or 1 to 4 carbon atoms. The radical centers of the alkylene can be on the same carbon atom (i.e., an alkylidene) or on different carbon atoms.

The term "aralkyl" refers to a monovalent group that is a radical of the compound R—Ar where Ar is an aromatic carbocyclic group and R is an alkyl group.

The term "aryl" refers to a monovalent group that is a radical of a carbocyclic aromatic compound. The aryl can have one aromatic ring or can include up to 5 other carbocyclic rings that are connected to or fused to the aromatic ring. The other carbocyclic rings can be aromatic, non-aromatic, or combination thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

The term "arylene" refers to a divalent group that is a radical of a carbocyclic aromatic compound. The arylene can have one aromatic ring or can include up to 5 other carbocyclic rings that are connected to or fused to the aromatic ring. The other carbocyclic rings can be aromatic, non-aromatic, or combination thereof. Exemplary arylene groups have 1, 2, or 3 aromatic rings. For example, the arylene group can be phenylene.

The term "azido" refers to a group of formula —N$_3$.

The term "aziridinyl" refers to a cyclic monovalent radical of aziridine having the formula

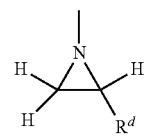

where R$^c$ is hydrogen or alkyl.

The term "benzotriazolyl" refers to a monovalent group having a benzene ring fused to a triazolyl group. The formula for a benzotriazolyl group is C$_6$H$_4$N$_3$—.

The term "carbonyl" refers to a divalent group of formula —(CO)—.

The term "carbonylimino" refers to a divalent group of formula —(CO)NR$^a$— where R$^a$ is hydrogen, alkyl, aryl, aralkyl, or part of a ring structure.

The term "carbonyloxy" refers to a divalent group of formula —(CO)O—.

The term "carbonyloxycarbonyl" refers to a divalent group of formula —(CO)O(CO)—. Such a group is part of an anhydride compound.

The term "carbonylthio" refers to a divalent group of formula —(CO)S—.

The term "carboxy" refers to a monovalent group of formula —(CO)OH.

The term "cyano" refers to a monovalent group of formula —CN.

The term "disulfide" refers to a divalent group of formula —S—S—.

The term "fluoroalkyl" refers to an alkyl having at least one hydrogen atom replaced with a fluorine atom. As used herein, the term "lower fluoroalkyl" refers to a fluoroalkyl having 1, 2, 3, or 4 carbon atoms. Some exemplary fluoroalkyls have one carbon atom such as —CHF$_2$ or —CF$_3$.

The term "fluoroalkoxy" refers to an alkoxy having at least one hydrogen atom replaced with a fluorine atom.

The term "fluoroalkoxycarbonyl" refers to a monovalent group of formula —(CO)OR$^f$ where (CO) refers to a carbonyl group and R$^f$ refers to a fluoroalkyl group.

The term "halo" refers to fluoro, bromo, chloro, or iodo.

The term "haloalkyl" refers to an alkyl having at least one hydrogen atom replaced with a halogen selected from F, Cl, Br, or I. Perfluoroalkyl groups are a subset of haloalkyl groups.

The term "halocarbonyl" refers to a monovalent group of formula —(CO)X where X is a halogen atom selected from F, Cl, Br, or I.

The term "halocarbonyloxy" refers to a monovalent group of formula —O(CO)X where X is a halogen atom selected from F, Cl, Br, or I.

The term "halosilyl" refers to a group having a Si attached to a halogen (i.e., Si—X where X is a halogen). For example, the halosilyl group can be of formula —SiX$_{3-n}$(L$^b$)$_n$ where n is an integer of 0 to 2 and L$^b$ is selected from an alkoxy or acyloxy. Some specific examples include the groups —SiCl$_3$, —SiCl$_2$OCH$_3$, and —SiCROCH$_3$)$_2$.

The term "heteroalkylene" refers to a divalent group that is an alkylene having one or more carbon atoms replaced with a sulfur, oxygen, or —NR$^c$— where R$^c$ is hydrogen or alkyl. The heteroalkylene can be linear, branched, cyclic, or combination thereof and can include up to 400 carbon atoms and up to 30 heteroatoms. In some embodiments, the heteroalkylene includes up to 300 carbon atoms, up to 200 carbon atoms, up to 100 carbon atoms, up to 50 carbon atoms, up to 30 carbon atoms, up to 20 carbon atoms, or up to 10 carbon atoms.

The term "hydroxy" refers to a group of formula —OH.

The term "isocyanato" refers to a group of formula —NCO.

The term "mercapto" refers to a group of formula —SH.

The term "oxy" refers to a divalent group of formula —O—.

The term "oxycarbonylimino" refers to a divalent group of formula —O(CO)NR$^a$— where R$^a$ is hydrogen, alkyl, aryl, or aralkyl.

The term "oxycarbonyloxy" refers to a divalent group of formula —O(CO)O—.

The term "oxycarbonylthio" refers to a divalent group of formula —O(CO)S—.

The term "phosphato" refers to a monovalent group of formula —OPO$_3$(R$^c$)$_2$ where R$^c$ is hydrogen or alkyl.

The term "phosphono" refers to a monovalent group of formula —PO$_3$(R$^c$)$_2$ that is attached to a carbon atom and where R$^c$ is hydrogen or alkyl.

The term "phosphoramido" refers to a monovalent group of formula —NHPO$_3$H$_2$.

The term "primary aromatic amino" refers to a monovalent group of formula —ArNH$_2$ where Ar is an aryl group.

The term "secondary aromatic amino" refers to a monovalent group of formula —ArNR$^b$H where Ar is an aryl group and R$^b$ is an alkyl or aryl.

The term "tertiary amino" refers to a group of formula —N(R$^b$)$_2$ attached to a carbon atom where R is an alkyl or aryl.

The term "thio" refers to a divalent group of formula —S—.

The term "amino-containing material" refers to a material that has a primary amino group or a secondary amino group. The amino-containing material can be a biological material or a non-biological material. The amino-containing material often has an alkylene group attached to the primary amino group or secondary amino group.

The term "attachment group" refers to the group formed by reaction of a substrate-reactive group (i.e., group X in a tethering compound according to Formula I) with a complementary functional group on the surface of a substrate.

The term "complementary functional group" refers to a group capable of reacting with a recited group to form an ionic bond, covalent bond, or combination thereof. The complementary functional group can be a group on a substrate capable of reacting with group X in a tethering compound according to Formula I. The complementary group is a group that is not equal to X. For example, a complementary group for an ethylenically unsaturated group is not another ethylenically unsaturated group that undergoes a free radical polymerization reaction but is a non-identical group capable of reacting with the ethylenically unsaturated group such as a silyl hydride or mercaptan.

The term "immobilization group" refers to a group connecting an amino-containing material to a substrate. The attachment group and a carbonylimino group are part of the immobilization group.

The term "room temperature" refers to a temperature of about 20° C. to about 25° C. or about 22° C. to about 25° C.

The term "substrate" refers to a solid phase support to which a tethering compound can be attached. The substrates can have any useful form including, but not limited to, thin films, sheets, membranes, filters, nonwoven or woven fibers, hollow or solid beads, bottles, plates, tubes, rods, pipes, or wafers. The substrates can be porous or non-porous, rigid or flexible, transparent or opaque, clear or colored, or reflective or non-reflective. Suitable substrate materials include, for example, polymeric materials, glasses, ceramics, metals, metal oxides, hydrated metal oxides, or combination thereof.

The term "tethering compound" refers to a compound that has two reactive groups such as compounds according to Formula I. One of the reactive groups (i.e., the substrate-reactive functional group) can react with a complementary functional group on the surface of a substrate to form a substrate-attached tethering group. The other reactive group (i.e., the fluoroalkoxycarbonyl group) can react with an amino-containing material. Reaction of both reactive groups of the tethering compound results in the formation of an immobilization group that connects the amino-containing material to the substrate.

The terms "tethering group" and "substrate-attached tethering group" are used interchangeably to refer to a group attached to a substrate that results from the reaction of a substrate-reactive group of the tethering compound with a complementary functional group on the surface of the substrate. The tethering group includes a fluoroalkoxycarbonyl group that can react with an amino-containing material.

The above summary of the present invention is not intended to describe each disclosed embodiment or every implementation of the present invention. The Figures and the detailed description that follow more particularly exemplify these embodiments.

DETAILED DESCRIPTION OF THE INVENTION

Methods for immobilizing an amino-containing material on a substrate and articles containing amino-containing material immobilized on a substrate are described. A tethering compound is used to connect the amino-containing material to the substrate. The tethering compound has two reactive groups: a substrate reactive group and a fluoroalkoxycarbonyl group. A substrate-attached tethering group is formed by reacting the substrate reactive group of the tethering compound with a complementary functional group on the surface of a substrate to form an ionic bond, covalent bond, or combination thereof. The substrate-attached tethering group contains a fluoroalkoxycarbonyl group. The fluoroalkoxycarbonyl group of the substrate-attached tethering group is reacted with a primary or secondary amino-containing material to form an immobilization group that connects the amino-containing material to the substrate.

The tethering compounds are of Formula I:

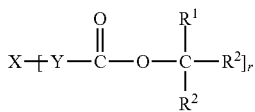

In Formula I, X is a substrate-reactive functional group selected from a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, disulfide, alkyl disulfide, benzotriazolyl, phosphono, phosphoroamido, phosphato, or ethylenically unsaturated group. Group Y is a single bond or a divalent group that includes an alkylene, heteroalkylene, arylene, or combination thereof. Optionally, when Y is a divalent group, Y can further include a carbonyl, carbonyloxy, carbonylimino, oxy, —$NR^3$— or combination thereof. Group $R^1$ is selected from hydrogen, fluoro, alkyl, or lower fluoroalkyl; and each group $R^2$ is a lower fluoroalkyl. Group $R^3$ is selected from hydrogen, alkyl, aryl, or aralkyl. The variable r is equal to 1 when X is a monovalent group or equal to 2 when X is a divalent group. The tethering compound of Formula I can be unsubstituted or substituted with a halo, alkyl, alkoxy, or combination thereof. The use of the term "combination thereof" with reference to the substituents of the tethering compounds means that multiple substituents can be present and any substituent can be independently selected from a halo, alkyl, or alkoxy.

The substrate reactive group X typically does not react with the fluoroalkoxycarbonyl group in Formula I and can be used to provide attachment to a substrate. That is, group X in tethering compounds of Formula I can react with a complementary functional group on the surface of the substrate to form a substrate-attached tethering group to form an ionic bond, covalent bond, or combination thereof. Group X can be monovalent or divalent. When X is monovalent, r in Formula I is equal to 1 and the compound has the following structure as shown in Formula Ia.

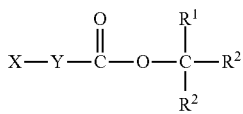

Suitable monovalent X groups include a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, alkyl disulfide, benzotriazolyl, phosphono, phosphoroamido, phosphato, or ethylenically unsaturated group. When X is divalent, r in Formula I is equal to 2 and the compound has the following structure as shown in Formula Ib.

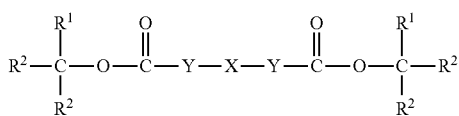

The compound can be symmetrical about X. A disulfide is an exemplary divalent X group.

The X group typically can react with a complementary functional group on the surface of a substrate to form an ionic bond, covalent bond, or combination thereof. Suitable X groups for attachment to the surface of a polymeric substrate include a carboxy, halocarbonyl, halocarbonyloxy, cyano, hydroxy, mercapto, isocyanato, halosilyl, alkoxysilyl, acyloxysilyl, azido, aziridinyl, haloalkyl, or tertiary amino. Suitable X groups for attachment to the surface of a gold-containing substrate include mercapto, disulfide, or alkyl disulfide. Suitable X groups for attachment to the surface of other metal-containing substrates include benzotriazolyl, phosphono, phosphoroamido, phosphato, or ethylenically unsaturated groups. Suitable X groups for attachment to glass or ceramic-containing substrates as well as to metal oxide-containing or hydrated metal oxide-containing substrates include halosilyl, alkoxysilyl, or acyloxysilyl groups.

The tethering compounds of Formula I include a fluoroalkoxycarbonyl group of formula —(CO)$OR^1(R^2)_2$ where $R^1$ is selected from hydrogen, fluoro, alkyl, or lower fluoroalkyl; and each $R^2$ is independently selected from a lower fluoroalkyl. Suitable alkyl groups for $R^1$ typically have 1 to 10, 1 to 6, or 1 to 4 carbon atoms. Suitable lower fluoroalkyl groups for $R^1$ and $R^2$ typically have 1 to 4 carbon atoms. Some exemplary lower fluoroalkyl groups have one carbon atom such as —$CHF_2$ or —$CF_3$.

In some exemplary tethering compounds, the fluoroalkoxycarbonyl group is selected from either —(CO)OCH$(CF_3)_2$ where $R^1$ is hydrogen and each $R^2$ is —$CF_3$ or —(CO)OC$(CF_3)_3$ where $R^1$ and each $R^2$ is —$CF_3$. In other exemplary tethering compounds, the fluoroalkoxycarbonyl group is selected from —(CO)OCF$(CF_3)_2$ where $R^1$ is fluoro and $R^2$ is —$CF_3$.

Group Y in the tethering compounds of Formula I is a single bond or a divalent group that includes an alkylene, heteroalkylene, arylene, or combination thereof. When Y is a divalent group, Y can optionally further include a carbonyl, carbonyloxy, carbonylimino, oxy, thio, —$NR^3$—, or combination thereof. Group $R^3$ is selected from hydrogen, alkyl, aryl, or aralkyl. Group Y typically does not contain a peroxy (i.e., —O—O—) linkage. When describing the group Y, the term "combination thereof" means that multiple groups can be linked together. For example, a first divalent group can be linked to a second divalent group or a first divalent group can be linked to a second divalent group that is also linked to a third divalent group.

In some embodiments, group Y can be an alkylene group or Y can include a first alkylene connected to at least one other group selected from a heteroalkylene, arylene, second alkylene, carbonyl, carbonyloxy, carbonylimino, oxy, thio, —$NR^3$—, or combination thereof. In other tethering compounds, Y can be a heteroalkylene group or Y can include a first heteroalkylene connected to at least one other group selected from an alkylene, arylene, second heteroalkylene, carbonyl, carbonyloxy, carbonylimino, oxy, thio, —$NR^3$—, or combination thereof. In still other tethering compounds, Y can be an arylene group or Y can include a first arylene connected to at least one other group selected from another alkylene, heteroalkylene, second arylene, carbonyl, carbonyloxy, carbonylimino, oxy, thio, —$NR^3$—, or combination thereof. The term "connected" or "linked" can either that the groups are directly or indirectly bonded to each other.

In some tethering compounds according to Formula I, Y is an alkylene group as shown in Formula Ic

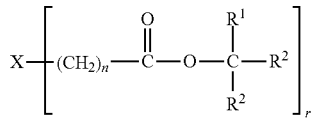

where n is an integer of 1 to 20. Exemplary compounds include those were n is an integer no greater than 15, no greater than 10, no greater than 8, no greater than 6, no greater than 4, no greater than 3, or no greater than 2.

In other tethering compounds according to Formula I, Y is a heteroalkylene group as shown in Formulas Id or Ie

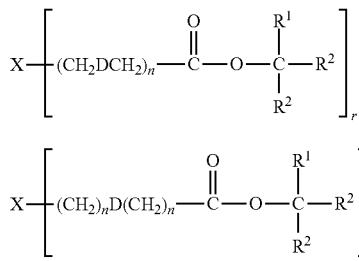

where n is an integer of 1 to 20 and D is oxy, thio, or —NH—. Exemplary tethering compounds include those where D is oxy and n is an integer no greater than 15, no greater than 10, no greater than 8, no greater than 6, no greater than 4, no greater than 3, or no greater than 2.

In still other tethering compounds according to Formula I, Y includes a first alkylene group that is linked to a second alkylene or a first heteroalkylene group with a group selected from a carbonyl, carbonyloxy, carbonylimino, oxy, thio, or —NR$^3$—. Additional alkylene or heteroalkylene groups can be linked to the second alkylene or to the first heteroalkylene group with a group selected from a carbonyl, carbonyloxy, carbonylimino, oxy, thio, or —NR$^3$—. In yet other exemplary tethering compounds of Formula I, Y includes a first heteroalkylene that is linked to a second heteroalkylene or to a first alkylene group with a group selected from a carbonyl, carbonyloxy, carbonylimino, oxy, thio, or —NR$^3$—. Additional alkylene or heteroalkylene groups can be linked to the second heteroalkylene or to the first alkylene group with a group selected from a carbonyl, carbonyloxy, carbonylimino, oxy, thio, or —NR$^3$—.

For instance, the tethering compounds can be of Formula If, Ih, or Ig.

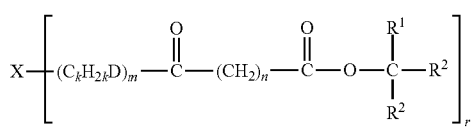

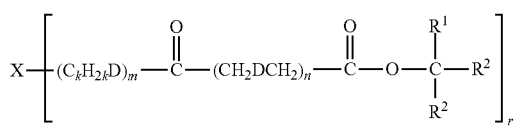

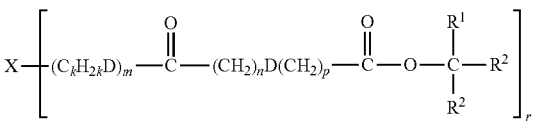

where D is oxy, thio, or —NH—; m is an integer of 1 to 15; k is an integer of 2 to 4; and n is an integer of 1 to 20. For example, both n and m can independently be an integer no greater than 15, no greater than 10, no greater than 8, no greater than 6, no greater then 4, no greater than 3, or no greater than 2. In many compounds of Formula Id, Id, or Ie, k is equal to 2, D is oxy, m is equal to 1, and n is an integer no greater than 3.

Several factors can influence the selection of group Y for a particular application. These factors include, for example, ease of synthesis of the tethering compound and reactivity or selectivity of the fluoroalkoxycarbonyl group with an amino-containing material. For example, the size and the polarity of group Y can affect the reactivity of the fluoroalkoxycarbonyl group with amino-containing material. That is, the reactivity of the fluoroalkoxycarbonyl group can be altered by varying the length of group Y, the composition of group Y, or both.

Exemplary compounds according to Formula I include, but are not limited to, the following:

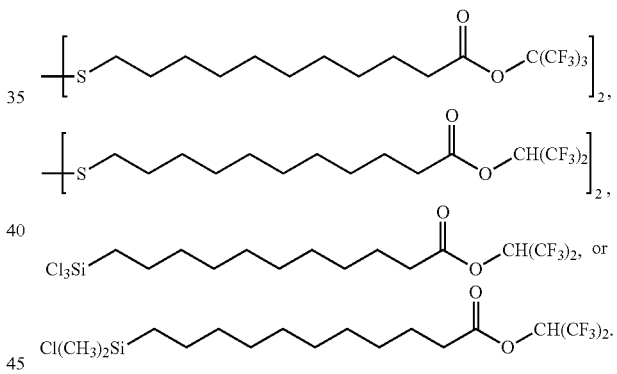

Any tethering compounds within the scope of Formula I can be unsubstituted or substituted with a halo, alkyl, alkoxy, or combination thereof. For example, any alkyl, aryl, aralkyl, heteroalkylene, alkylene, or arylene group can be further substituted with a halo, alkyl, alkoxy, or combination thereof.

The compounds of Formula I can be prepared by any method known to those of skill in the art. For example, where X is a disulfide, a compound having two carboxy groups can be converted to a compound having two halocarbonyl groups. More specifically, a compound of formula HO(CO)—Y—X—Y—(CO)OH can be converted to compound of formula Cl(CO)—Y—X—Y—(CO)Cl by reaction with thionyl chloride. The halocarbonyl groups can then be reacted with an alcohol of formula HOCR$_1$(R$_2$)$_2$ in the presence of an acid acceptor where R$^1$ and R$^2$ are defined above. Alternatively, the halocarbonyl groups can be reacted with a (R$^2$)$_2$CFO$^-$K$^+$, which is the adduct of KF and a perfluoroketone formed in situ. Alternatively, the intermediate fluorinated ester can be prepared and then reacted to provide the attached X group. For example, a compound having a carbon-carbon double bond and a carboxy group can be reacted with thionyl chloride to form a compound having a carbon-carbon double bond and a halocarbonyl group. The halocarbonyl group can be reacted as described above to form the ester. The carbon-carbon double bond can then be reacted to provide the X group. For example, X equal to a halosilyl can be prepared by reacting $HSiCl_3$ with the carbon-carbon double bond in the presence of a catalyst.

The method of immobilizing an amino-containing material includes reacting substrate-reactive group X of the tethering compound with a complementary group on the surface of a substrate to form a substrate-attached tethering group. The substrate-attached tethering group has a fluoroalkoxycarbonyl group that can react with a primary or secondary amino-containing material to form an immobilization group that connects the amino-containing material to a substrate.

The overall reaction of the tethering compound with a complementary group G on the surface of a substrate to form a substrate-attached tethering group and of the substrate-attached tethering group with a primary amino-containing material or secondary amino-containing material is shown in Reaction Scheme C.

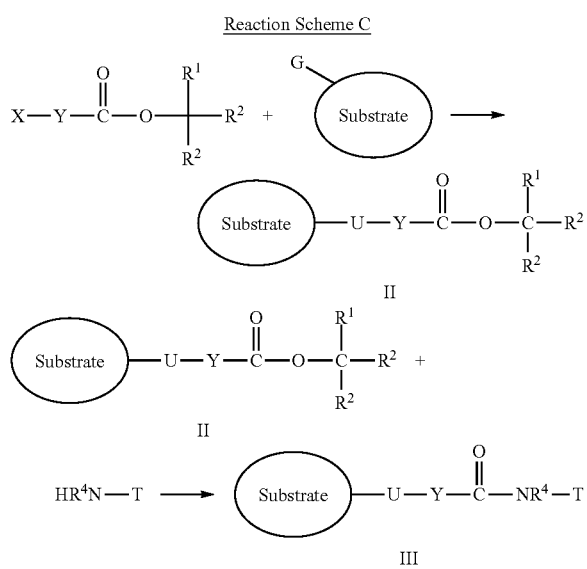

Formula II can represent a tethering group attached to a substrate where r in Formula I is equal to 1. That is, Formula II can represent a substrate-attached tethering group, which is the reaction product of a complementary functional group G on a surface of a substrate with group X of a tethering compound of Formula I. Complementary groups on a substrate (i.e., groups G) capable of reacting with X groups in compounds according to Formula I include, but are not limited to, hydroxy, mercapto, primary aromatic amino group, secondary aromatic amino group, secondary aliphatic amino group, azido, carboxy, carbonyloxycarbonyl, isocyanate, halocarbonyl, halocarbonyloxy, silanol, silyl hydride, and nitrile. Group U is the attachment group formed by reaction of X in a tethering compound according to Formula I with group G on the surface of a substrate (i.e., group U is the reaction product of group G on the surface of the substrate and group X of the tethering compound). The groups Y, $R^1$, and $R^2$ are the same as previously defined for Formula I. The tethering group can be unsubstituted or substituted with a halo, alkyl, alkoxy, or combination thereof.

Formula II shows only one tethering group attached to the substrate; however, more than one tethering group can be attached to the substrate if there are more than one reactive group G on the substrate. Further, the substrate can have excess G groups on the surface of the substrate that have not reacted with a tethering compound.

The fluoroalkoxycarbonyl group (i.e., —(CO)—O—$CR^1$ $(R^2)_2$ group) of the substrate-attached tethering group of Formula II can react with an amino-containing material of formula $HR^4$N-T to connect the amino-containing material to the substrate as shown in Formula III. The amino-containing material is a primary amino-containing material, a secondary amino-containing material, or a combination thereof (e.g., a material can have both a primary amino group and a secondary amino group). Group $R^4$ is selected from hydrogen, alkyl, or a portion of a ring structure connected to group T. Group T is the remainder of the primary or secondary amino-containing material (i.e., the group T is equal to an amino-containing material of formula $HR^4$N-T minus the $HR^4$N— group). Group T often has an alkylene group adjacent to the amino group.

More specifically, the amino-containing material can react by a nucleophilic substitution reaction with the fluoroalkoxycarbonyl group of the substrate-attached tethering group. An immobilization group of formula —U—Y—(CO)—$NR^4$-T is formed resulting in the connection of the amino-containing material to the substrate. Formula III shows only one immobilization group of formula —U—Y—(CO)—$NR^4$-T attached to the substrate. However, there can be multiple groups of formula —U—Y—(CO)—$NR^4$-T attached to the substrate. In Formula III, U is the attachment group as described for Formula II; and Y is the same as previously defined for Formulas I and II.

If a substrate has multiple tethering groups containing a fluoroalkoxycarbonyl group and an amino-containing material has multiple primary and/or secondary amino groups, the amino-containing material can react with more than one tethering group. That is, an amino-containing material having a plurality of primary and/or secondary amino groups can function to crosslink multiple immobilization groups.

In many embodiments, not all of the substrate-attached tethering groups of formula —U—Y—(CO)—$OCR^1(R^2)_2$ are reacted with the amino-containing material. That is, only a portion of the tethering groups containing a fluoroalkoxycarbonyl group are reacted with an amino-containing material. There is an excess of the tethering groups that contain a fluoroalkoxycarbonyl group. An excess of these tethering groups may be desirable because it tends to favor the reactivity of any amino-containing materials that may be present.

More specifically, an article can include a substrate with (a) an attached tethering group of Formula IV

—U—Y—(CO)—$OCR^1(R^2)_2$                 (IV)

that includes a fluoroalkoxycarbonyl group and (b) an attached immobilization group of Formula V.

—U—Y—(CO)—$NR^4$-T                        (V)

The group U is equal to the reaction product of a substrate-reactive functional group X and a complementary group G on the surface of the substrate, as described previously. Groups Y, $R^1$, and $R^2$ are the same as described for Formula I. Group T is equal to the remainder of a primary or secondary amino-containing material of formula T-$NHR^4$ absent the amino group —NHR$^4$. Group R$^4$ is selected from hydrogen, alkyl, or a portion of a ring structure connected to group T. The amino group —NR$^4$ is often connected to an alkylene group in the remainder of the amino-containing material.

Some substrates that have an attached tethering group of Formula IV as well as an attached immobilization group of Formula V also have a unreacted complementary group G.

Suitable substrates are described previously. The tethering group of Formula IV can be formed by the reaction of a tethering compound of Formula I with a substrate. The immobilization group of Formula V is the reaction product of an amino-containing material having a primary or secondary amino group with a substrate-attached tethering group of Formula IV.

The substrate, which contains the complementary functional groups G in Reaction Scheme C, is usually a solid phase material to which the tethering groups and immobilization groups can be attached. The substrate is not soluble in a solution used to attach a compound of Formula I to the surface of the substrate. Typically, a tethering group or immobilization group is attached only to an outer portion of the substrate and a bulk portion of the substrate is not modified during the process of attaching the tethering group to the substrate. If the substrate has groups G distributed throughout the substrate, only those groups G in the outer portion (e.g., on or near the surface) are usually capable of reacting with group X of the compounds according to Formula I to form a substrate-attached tethering group of Formula II.

The substrates can have any useful form including, but not limited to, thin films, sheets, membranes, filters, nonwoven or woven fibers, hollow or solid beads, bottles, plates, tubes, rods, pipes, or wafers. The substrates can be porous or non-porous, rigid or flexible, transparent or opaque, clear or colored, and reflective or non-reflective. Suitable substrate materials include, for example, polymeric materials, glasses, ceramics, metals, metal oxides, hydrated metal oxides, or a combination thereof.

The substrates can have a single layer or multiple layers of material. For example, the substrate can have one or more second layers that provide support for a first layer that includes a complementary functional group G capable of reacting with the X group in tethering compounds of Formula I. The first layer is the outer layer of the substrate. In some embodiments, a surface of a second layer is chemically modified or coated with another material to provide a first layer that includes a complementary functional group capable of reacting with the X group.

Suitable polymeric substrate materials include, but are not limited to, polyolefins, polystyrenes, polyacrylates, polymethacrylates, polyacrylonitriles, polyvinyl acetates, polyvinyl alcohols, polyvinyl chlorides, polyoxymethylenes, polycarbonates, polyamides, polyimides, polyurethanes, phenolics, polyamines, amino-epoxy resins, polyesters, silicones, cellulose based polymers, polysaccharides, or combination thereof. In some embodiments, the polymeric material is a copolymer prepared using a comonomer having a complementary functional group capable of reacting with a group X in tethering compounds according to Formula I. For example, the comonomer can contain a carboxy, mercapto, hydroxy, amino, or alkoxysilyl group.

Suitable glass and ceramic substrate materials can include, for example, sodium, silicon, aluminum, lead, boron, phosphorous, zirconium, magnesium, calcium, arsenic, gallium, titanium, copper, or combination thereof. Glasses typically include various types of silicate containing materials.

In some embodiments, the substrate includes a layer of diamond-like glass as discussed in U.S. Pat. No. 6,696,157 (David et al.). The diamond-like glass is an amorphous material that includes carbon, silicon, and one or more elements selected from hydrogen, oxygen, fluorine, sulfur, titanium, or copper. Some diamond-like glass materials are formed from a tetramethysilane precursor using a plasma process. A hydrophobic material can be produced that is further treated using an oxygen plasma to control the silanol concentration on the surface.

Diamond-like glass can be in the form of a thin film or in the form of a coating on another layer or material in the substrate. In some applications, the diamond-like glass can be in the form of a thin film having at least 30 weight percent carbon, at least 25 weight percent silicon, and up to 45 weight percent oxygen. Such films can be flexible and transparent. In some embodiments, the diamond-like glass is the outer layer of a multilayer substrate. In a specific example, the second layer (e.g., support layer) of the substrate is a polymeric material and the first layer is a thin film or layer of diamond-like glass. The tethering group is attached to the surface of the diamond-like glass.

In some multilayer substrates, the diamond like glass is deposited on a layer of diamond-like carbon. For example, the second layer (e.g., support layer) is a polymeric film having a layer of diamond-like carbon deposited on a surface. A layer of diamond-like glass is deposited over the diamond-like carbon layer. The diamond-like carbon can, in some embodiments, function as a tie layer or primer layer between a polymeric layer and a layer of diamond-like glass in a multilayer substrate. For example, the multilayer substrate can include a polyimide or polyester layer, a layer of diamond-like carbon deposited on the polyimide or polyester, and a layer of diamond-like glass deposited on the diamond-like carbon. In another example, the multilayer substrate includes a stack of the layers arranged in the following order: diamond-like glass, diamond-like carbon, polyimide or polyester, diamond-like carbon, and diamond-like glass.

Diamond-like carbon films can be prepared, for example, from acetylene in a plasma reactor. Other methods of preparing such films are described in U.S. Pat. Nos. 5,888,594 and 5,948,166, as well as in the article M. David et al., *AIChE Journal,* 37 (3), 367-376 (March 1991).

Suitable metals, metal oxides, or hydrated metal oxides for substrates can contain, for example, gold, silver, platinum, palladium, aluminum, copper, chromium, iron, cobalt, nickel, zinc, and the like. The metal-containing material can be alloys such as stainless steel, indium tin oxide, and the like. In some embodiments, a metal-containing material is the top layer of a multilayer substrate. For example, the substrate can have a polymeric second layer and a metal containing first layer. In one example, the second layer is a polymeric film and the first layer is a thin film of gold. In other examples, a multilayer substrate includes a polymeric film coated with a titanium-containing layer and then coated with a gold-containing layer. That is, the titanium layer can function as a tie layer or a primer layer for the adhesion of the layer of gold to the polymeric film.

In other examples of a multilayer substrate, a silicon support layer is covered with a layer of chromium and then with a layer of gold. The chromium layer can improve the adhesion of the gold layer to the silicon layer.

The surface of the substrate typically includes a group capable of reacting with a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, disulfide, alkyl disulfide, benzotriazolyl, phosphono, phosphoroamido, phosphato, or ethylenically unsaturated group. That is, the surface of the substrate includes a group capable of reacting with the group X in compounds of Formula I (i.e., the substrate includes a functional group G that is complementary to the group X). Substrates can include a support material that is treated to have an outer layer that includes a complementary functional group. The substrate can be prepared from any solid phase material known to have groups capable of reacting with X and is not limited to the following examples of suitable materials.

A carboxy group or a halocarbonyl group can react with a substrate having a hydroxy group to form a carbonyloxy-containing attachment group. Examples of substrate materials having hydroxy groups include, but are not limited to, polyvinyl alcohol, corona-treated polyethylene, hydroxy substituted esters of polymethacrylates, hydroxy substituted esters of polyacrylates, and a polyvinyl alcohol coating on a support material such as glass or a polymeric material.

A carboxy group or a halocarbonyl group can also react with a substrate having a mercapto group to form a carbonylthio-containing attachment group. Examples of substrate materials having a mercapto group include, but are not limited to, mercapto substituted esters of polyacrylates, mercapto substituted esters of polymethacrylates, and glass treated with a mercaptoalkylsilane.

Additionally, a carboxy group or a halocarbonyl group can react with a primary aromatic amino group, a secondary aromatic amino group, or a secondary aliphatic amino group to form a carbonylimino-containing attachment group. Examples of substrate materials having aromatic primary or secondary amino groups include, but are not limited to, polyamines, amine substituted esters of polymethacrylate, amine substituted esters of polyacrylate, polyethylenimines, and glass treated with an aminoalkylsilane.

A halocarbonyloxy group can react with a substrate having a hydroxy group to form an oxycarbonyloxy-containing attachment group. Examples of substrate materials having hydroxy groups include, but are not limited to, polyvinyl alcohol, corona-treated polyethylene, hydroxy substituted esters of polymethacrylates, hydroxy substituted esters of polyacrylates, and a polyvinyl alcohol coating on a support material such as glass or a polymeric film.

A halocarbonyloxy group can also react with a substrate having a mercapto group to form an oxycarbonylthio-containing attachment group. Examples of substrate materials having a mercapto group include, but are not limited to, mercapto substituted esters of polymethacrylates, mercapto substituted esters of polyacrylates, and glass treated with a mercaptoalkylsilane.

Additionally, a halocarbonyloxy group can react with a substrate having a primary aromatic amino group, a secondary aromatic amino group, or a secondary aliphatic amino group to form an oxycarbonylimino-containing attachment group. Examples of substrate materials having aromatic primary or secondary amino groups include, but are not limited to, polyamines, amine substituted esters of polymethacrylate, amine substituted esters of polyacrylate, polyethylenimines, and glass treated with an aminoalkylsilane.

A cyano group can react with a substrate having an azido group to form a tetrazinediyl-containing attachment group. Examples of substrates having azido groups include, but are not limited to, a coating of poly(4-azidomethylstyrene) on a glass or polymeric support. Suitable polymeric support materials include polyesters, polyimides, and the like.

A hydroxy group can react with a substrate having isocyanato groups to form an oxycarbonylimino-containing attachment group. Suitable substrates having isocyanato groups include, but are not limited to, a coating of 2-isocyanatoethylmethacrylate polymer on a support material. Suitable support materials include glass and polymeric materials such as polyesters, polyimides, and the like.

A hydroxy group can also react with a substrate having a carboxy group, carbonyloxycarbonyl group, or halocarbonyl group to form a carbonyloxy-containing attachment group. Suitable substrates include, but are not limited to, a coating of acrylic acid polymer or copolymer on a support material or a coating of a methacrylic acid polymer or copolymer on a support material. Suitable support materials include glass and polymeric materials such as polyesters, polyimides, and the like. Other suitable substrates include copolymers of polyethylene with polyacrylic acid, polymethacrylic acid, or combination thereof.

A mercapto group can react with a substrate having isocyanato groups. The reaction between a mercapto group and an isocyanato group forms a thiocarbonylimino-containing attachment group. Suitable substrates having isocyanato groups include, but are not limited to, a coating of 2-isocyanatoethylmethacrylate copolymer on a support material. Suitable support materials include glass and polymeric materials such as polyesters, polyimides, and the like.

A mercapto group can also react with a substrate having a halocarbonyl group to form a carbonylthio-containing attachment group. Substrates having halocarbonyl groups include, for example, chlorocarbonyl substituted polyethylene.

A mercapto group can also react with a substrate having a halocarbonyloxy group to form an oxycarbonlythio-containing attachment group. Substrates having halocarbonyl groups include chloroformyl esters of polyvinyl alcohol.

Additionally, a mercapto group can react with a substrate having an ethylenically unsaturated group to form a thioalkylene-containing attachment group. Suitable substrates having an ethylenically unsaturated group include, but are not limited to, polymers and copolymers derived from butadiene.

An isocyanato group can react with a substrate having a hydroxy group to form a oxycarbonylimino-containing attachment group. Examples of substrate materials having hydroxy groups include, but are not limited to, polyvinyl alcohol, corona-treated polyethylene, hydroxy substituted esters of polymethacrylates or polyacrylates, and a polyvinyl alcohol coating on glass or a polymeric material.

An isocyanato group can also react with a mercapto group to form a thiocarbonylimino-containing attachment group. Examples of substrate materials having a mercapto group include, but are not limited to, mercapto substituted esters of polymethacrylates or polyacrylates and glass treated with a mercaptoalkylsilane.

Additionally, an isocyanato group can react with a primary aromatic amino group, a secondary aromatic amino group, or a secondary aliphatic amino group to form a iminocarbonylimino-containing attachment group. Suitable substrates having a primary or secondary aromatic amino group include, but are not limited to, polyamines, polyethylenimines, and coatings of an aminoalkylsilane on a support material such as glass or on a polymeric material such as a polyester or polyimide.

An isocyanato group can also react with a carboxylic acid group to form an O-acyl carbamoyl-containing attachment group. Suitable substrates having a carboxylic acid group include, but are not limited to, a coating of an acrylic acid polymer or copolymer or a coating of a methacrylic acid polymer or copolymer on a glass or polymeric support. Copolymers include, but are not limited to, copolymers that contain polyethylene and polyacrylic acid or polymethacrylic acid. Suitable polymeric support materials include polyesters, polyimides, and the like.

A halosilyl group, an alkoxysilyl group, or an acyloxysilyl group can react with a substrate having a silanol group to form a disiloxane-containing attachment group. Suitable substrates include those prepared from various glasses, ceramic materials, or polymeric material. These groups can also react with various materials having metal hydroxide groups on the surface to form a silane-containing linkage. Suitable metals include, but are not limited to, silver, aluminum, copper, chromium, iron, cobalt, nickel, and zinc. In some embodiments, the metal is stainless steel or another alloy. Polymeric material can be prepared to have silanol groups. For example, commercially available monomers with silanol groups include 3-(trimethoxysilyl)propyl methacrylate and 3-aminoproplytrimethoxysilane, which are available from Aldrich Chemical Co., Milwaukee, Wis.

An azido group can react, for example, with a substrate having a carbon-carbon triple bond to form a triazolediyl-containing attachment group. An azido group can also react with a substrate having nitrile groups to form a tetrazenediyl-containing attachment group. Substrates having nitrile groups include, but are not limited to, coatings of polyacrylonitrile on a support material such as glass or a polymeric material. Suitable polymeric support material includes polyesters and polyimides, for example. Other suitable substrates having nitrile groups include acrylonitrile polymers or copolymers and 2-cyanoacrylate polymers or copolymers.

An azido group can also react with a strained olefinic group to form a triazolediyl-containing attachment group. Suitable substrates have a strained olefinic group include coatings that have pendant norbornenyl functional groups. Suitable support materials include, but are not limited to, glass and polymeric materials such as polyesters and polyimides.

An aziridinyl group can react with a mercapto group to form a β-aminoalkylthioalkylene-containing attachment group. Examples of substrate materials having a mercapto group include, but are not limited to, mercapto substituted esters of polymethacrylates or polyacrylates and glass treated with a mercaptoalkylsilane.

Additionally, an aziridinyl group can react with a carboxylic acid group to form a β-aminoalkyloxycarbonyl-containing attachment group. Suitable substrates having a carboxy include, but are not limited to, a coating of a acrylic acid polymer or copolymer, or a coating of a methacrylic acid polymer or copolymer on a glass or polymeric support. Copolymers include, but are not limited to, copolymers that contain polyethylene and polyacrylic acid or polymethacrylic acid. Suitable polymeric support materials include polyesters, polyimides, and the like.

A haloalkyl group can react, for example, with a substrate having a tertiary amino group to form a quaternary ammonium-containing attachment group. Suitable substrates having a tertiary amino group include, but are not limited to, polydimethylaminostyrene or polydimethylaminoethylmethacrylate.

Likewise, a tertiary amino group can react, for example, with a substrate having a haloalkyl group to form a quaternary ammonium-containing attachment group. Suitable substrates having a haloalkyl group include, for example, coatings of a haloalkylsilane on a support material. Support materials can include, but are not limited to, glass and polymeric materials such as polyesters and polyimides.

A disulfide or an alkyl disulfide group can react, for example, with a metal surface to form a metal sulfide-containing attachment group. Suitable metals include, but are not limited to gold, platinum, palladium, nickel, copper, and chromium. The substrate can also be an alloy such an indium tin oxide or a dielectric material.

A benzotriazolyl can react, for example, with a substrate having a metal or metal oxide surface. Suitable metals or metal oxides include, for example, silver, aluminum, copper, chromium, iron, cobalt, nickel, zinc, and the like. The metals or metal oxides can include alloys such as stainless steel, indium tin oxide, and the like.

A phosphono, phosphoroamido, or phosphato can react, for example, with a substrate having a metal or metal oxide surface. Suitable metals or metal oxides include, for example, silver, aluminum, copper, chromium, iron, cobalt, nickel, zinc, and the like. The metals or metal oxides can include alloys such as stainless steel, indium tin oxide, and the like.

An ethylenically unsaturated group can react, for example, with a substrate having an alkyl group substituted with a mercapto group. The reaction forms a heteroalkylene-containing attachment group. Suitable substrates include, for example, mercapto-substituted alkyl esters of polyacrylates or polymethacrylates.

An ethylenically unsaturated group can also react with a substrate having a silicon surface, such as a silicon substrate formed using a chemical vapor deposition process. Such silicon surfaces can contain a silyl hydride group (i.e., —SiH) that can react with the ethylenically unsaturated group in the presence of a platinum catalyst to form an attachment group with Si bonded to an alkylene group.

The tethering compounds of Formula I can undergo a self-assembly process when positioned in contact with a substrate. The term "self-assembly" refers to a process in which a material can spontaneously form a monolayer of substrate-attached tethering groups when contacted with a substrate. For example, compounds having a disulfide or alkyl disulfide X group can undergo a self-assembly process when exposed to a gold substrate. As another example, compounds having a halosilyl X group can undergo a self-assembly process when exposed to a diamond-like glass or glass substrate.

The attachment of tethering groups to the surface of a substrate (i.e., formation of the substrate-attached tethering groups of Formula II) can be detected using techniques such as, for example, contact angle measurements of a liquid on the substrate before and after attachment of a tethering group derived from Formula I (e.g., the contact angle can change upon attachment of a tethering group to the surface of a substrate), ellipsometry (e.g., the thickness of the attached layer can be measured), time-of-flight mass spectrometry (e.g., the surface concentration can change upon attachment of a tethering group to a substrate), and Fourier Transform Infrared Spectroscopy (e.g., the reflectance and absorbance can change upon attachment of a tethering group to a substrate).

The substrate-attached tethering group has a fluoroalkoxycarbonyl group that can react with a primary or secondary amino-containing material. In some embodiments, the amino-containing material is a biomolecule such as, for example, amino acid, peptide, DNA, RNA, protein, enzyme, organelle, immunoglobin, or fragments thereof. In other embodiments, the amino-containing material is a non-biological amine such as an amino-containing analyte. Other materials can be bound to the amino-containing material. For example, a complementary RNA or DNA fragment can hybridize with an immobilized RNA or DNA fragment. Biological amino-containing materials often can remain active after attachment to the substrate (i.e., the articles according to Formula III can include biologically active amino-containing materials immobilized to the substrate). For example, an immobilized antibody can bind with antigen or an immobilized antigen can bind with an antibody. An amino-containing material can bind to a bacterium (e.g., the immobilized amino-containing material can be a biomolecule that has a portion that can specifically bind to the bacterium). In a more specific example, the immobilized amino-containing material can bind to a *Staphylococcus aureus* bacterium.

The presence of the immobilized amino-containing material can be determined, for example, using mass spectrometry, contact angle measurement, infrared spectroscopy, and ellipsometry. Additionally, various immunoassays and optical microscopic techniques can be used if the amino-containing material is a biologically active material.

Immobilized biological amino-containing materials can be useful in the medical diagnosis of a disease or genetic defect. The immobilized amino-containing materials can also be used for biological separations or for detection of the presence of various biomolecules. Additionally, the immobilized amino-containing materials can be used in bioreactors or as biocatalysts to prepare other materials. The substrate-attached tethering groups can be used to detect amino-containing analytes.

The substrate-attached tethering groups of Formula II typically have improved hydrolytic stability (e.g., at pH equal to about 10) compared to previously known articles prepared using a tethering compound that is a derivative of N-hydroxysuccinimide. Further, the substrate-attached tethering groups of Formula II typically have improved hydrolytic stability compared to other previously known articles prepared using an azlactone compound or a perfluorophenyl ester. Because of the hydrolytic stability, the tethering compounds of Formula I and the substrate-attached tethering groups of Formula II can typically be used in aqueous systems. Still further, the substrate-attached tethering group of Formula II typically has improved reactivity toward amines compared to that of trifluoroethyl ($-CH_2CF_3$) esters.

When an amino-containing material reacts with a fluoroalkylcarbonyl group of the substrate-attached tethering group, an immobilization group is formed that results in the connection of the amino-containing material to the substrate (i.e., a substrate immobilized amino-containing materials according to Formulas III if formed). The rate of reaction of amino-containing materials with the fluoroalkoxycarbonyl groups of the substrate-attached tethering groups is typically faster than the rate of hydrolysis of the fluoroalkoxycarbonyl group. That is, immobilization of amino-containing materials occurs at a faster rate than the hydrolysis reactions. The amino-containing materials are not easily displaced once connection to a substrate has occurred due to the formation of a covalent carbonylimino bond.

EXAMPLES

These examples are merely for illustrative purposes only and are not meant to be limiting on the scope of the appended claims. All parts, percentages, ratios, etc. in the examples and the rest of the specification are by weight, unless noted otherwise. Solvents and other reagents used were obtained from Sigma-Aldrich Chemical Company; Milwaukee, Wis. unless otherwise noted.

| Table of Abbreviations | |
|---|---|
| Abbreviation or Trade Designation | Description |
| DTUA | 11,11'-dithiobisundecanoic acid |
| NHS | N-hydroxysuccinimide |
| Gold Films | Gold films of 2,000 Angstrom thickness commercially available from Platypus Technologies, Madison, WI. |
| SAM | Self Assembled Monolayer |
| Pt/DVTMDS | Platinum-vinyltetramethyldisiloxane, 15% in toluene |
| DMF | Dimethylformamide |
| THF | Tetrahydrofuran |
| TWEEN-25 | Polyoxyethylenesorbitan monolaurate from Sigma, St Louis, MO |

TEST METHODS

Half-Lives for Hydrolytic Stability

Half-lives for the hydrolytic stability of amine-reactive capture chemistries of SAMs on gold film were measured by RA-FTIR (Reflectance Absorbance Fourier Transform Infrared) on a BioRad Spectrometer using a liquid nitrogen cooled mercury-cadmium-telluride detector with a reflection apparatus set at 84°. The spectra were collected using 400 scans with a resolution of 2 $cm^{-1}$. A SAM formed from deuterated hexadecanethiol was used to collect the reference spectrum. The hydrolytic stability was measured by immersing the SAMs-coated gold film into carbonate buffer at pH 10 for up to 48 hours. At set time intervals, the SAMs-coated gold film were removed from the buffered solution and an RA-FTIR was taken where the intensity of the carbonyl peak at 1782±2 $cm^{-1}$ was measured.

Measurement of IgG Capture by Fluorescence:

Five microliter spots of the Cy5-IgG test solutions with the concentrations of 130, 50, 13, 5 and 0 micrograms per milliliter were applied to the coated surface and allowed to sit for 30 minutes. The surface was rinsed with 0.25 weight percent TWEEN-25 in DI water and then with DI water. The surfaces were dried under nitrogen and placed into a fluorescence reader, which is commercially available from Tecan Group LTD, Research Triangle Park, N.C. under the trade designation LS SERIES TECAN. Single scan measurements were made by adjusting the focal height to 1002 micrometers and using 40 micrometers resolution, a gain of 195, oversampling of 3 micrometers, and a pinhole depth focus of ±150 micrometers. The data was analyzed as 16-bit pixelized TIFF files using software commercially available from Molecular Devices Corp, Sunnyvale, Calif. under the trade designation GENEPIX PRO.

Preparation of IgG Labeled with Cy5

The contents of three vials of Cy5 dye (3H-Indolium, 2-[5-[1-[6-[(2,5-dioxo-1-pyrrolidinyl)oxy]-6-oxohexyl]-1,3-dihydro-3,3-dimethyl-5-sulfo-2H-indol-2-ylidene]-1,3-pentadienyl]-1-ethyl-3,3-dimethyl-5-sulfo-, inner salt (9CI)) were dissolved in dimethylsulfoxide (DMSO) to a total volume of 100 microliters. The vials of Cy5 dye were obtained from GE-Amersham Biosciences, Piscataway N.J. The resulting dye solution was added to 1 milliliter of a 5 milligrams/milliliter solution of mouse IgG in 0.1 M sodium carbonate (at pH 9.0). The mouse IgG was obtained from Sigma, St. Louis, Mo. The resulting solution was protected from light exposure and gently rocked for 45 minutes at room temperature. This solution contained Cy5-labelled antibody and unreacted Cy5.

Cy5-labelled antibody (Cy5-IgG) was separated from unreacted Cy5 label using gel filtration chromatography. The solution containing the Cy5-IgG and unreacted Cy5 was added to a PD-10 column that was equilibrated using phosphate buffer solution (PBS) at pH 7.4. The PD-10 column was obtained from GE-Amersham Biosciences, Piscataway N.J. The Cy5-IgG fraction was collected by washing with PBS at pH 7.4. The Cy5/IgG ratio was calculated by measuring the IgG concentration (280 nm) and the Cy5 concentration (650 nm) in the Cy5-IgG fraction. The product specifications provided by the manufacturer of Cy5 and IgG were followed to obtain the extinction coefficient values for IgG and Cy5 as well as the absorbance contribution from covalently bound Cy5 at 280 nm. The final Cy5-IgG solution had a concentration 1.3 milligrams/milliliter Cy5-IgG with a Cy5/IgG ratio of 2.2.

Preparative Example 1

Preparation of Disulfide N-Undecanoyl Hexafluoro-Iso-Propyl Ester

DTUA (0.50 gram) was converted to the diacid chloride by reaction with thionyl chloride (0.15 gram) in 3 milliliters $CH_2Cl_2$ containing a trace of DMF. To this material was added dry THF (2.0 milliliters) and a mixture of hexafluoro-iso-propanol (0.208 gram), ethyl diisopropyl amine (0.17 gram) and THF (0.81 gram). The mixture was stirred overnight, washed with water and filtered to isolate the solid product (0.502 grams). The structure was confirmed by NMR.

Preparative Example 2

Preparation of PEG Modified Disulfide N-Undecanoyl Hexafluoroisopropyl Ester

DTUA diacid chloride (10.9 grams) prepared as described in Preparative Example 1 was dissolved in $CH_2Cl_2$ (30 milliliters) and this solution was added to a solution of 2-aminoethoxyethanol (9.67 grams) in 30 milliliters of $CH_2Cl_2$. The diamide diol product (12.59 grams) was recovered by recrystallization from acetonitrile. This diol (3.00 grams) was mixed with succinic anhydride (1.08 grams) and triethylamine (1.15 grams) and heated to 90° C. to form a dark liquid. IR analysis showed complete reaction in a few hours and the product was cooled and recrystallized from acetonitrile to give 3.43 grams. The acid (0.50 grams) was dissolved in 3 milliliters of $CH_2Cl_2$ containing a trace of DMF and treated with thionyl chloride (0.15 gram). The solvent was removed using a rotary evaporator and the diacyl chloride was dissolved in 2 milliliters of THF. A solution of hexafluoroisopropanol (0.208 gram) and ethyl diisopropyl amine (0.17 gram) in 0.8 gram of THF was added. After overnight, the mixture was washed with water and the solid product collected and dried to 0.502 gram. The structure was confirmed by NMR.

Preparative Example 3

Preparation of Disulfide N-Undecanoyl N-Hydroxysuccinimide Ester

To the diacid chloride of DTUA (prepared by the reaction of DTUA (2.00 grams) with thionyl chloride (1.15 grams) in $CH_2Cl_2$ (12.6 grams) containing a trace of DMF) was added a mixture of NHS (1.11 grams), pyridine (0.80 gram) and $CH_2Cl_2$ (3 milliliters). The mixture was stirred overnight. The solvent was removed with a rotary evaporator, the resulting solid was washed with water and recrystallized from iso-propanol. The structure was confirmed by NMR.

Preparative Example 4

Preparation of Disulfide N-Undecanoyl Pentafluorophenyl Ester

To the diacid chloride of DTUA (0.50 gram) (prepared as described in Preparative Example 1) was added $CHCl_3$ (2.0 grams) and pentafluorophenol (0.14 gram) and pyridine (0.1 gram). The mixture was stirred overnight, the $CHCl_3$ was removed on a rotary evaporator, the residue was washed with an isopropanol/water mixture and filtered to give a solid product. The composition was confirmed by NMR.

Preparative Example 5

Preparation of hexafluoro-iso-propyl-11-(trichlorosilyl)undecanoate

Undecylenyl chloride (10.1 grams) was dissolved in 50 milliliters of $CH_2Cl_2$, hexafluoroisopropanol (9.5 grams) was added to it followed by the dropwise addition of diisopropylethylamine (6.6 grams), using an ice bath to moderate the exotherm. The product was washed twice with water, dried, and solvent was removed with a rotary evaporator to yield 13.4 grams of undecylenyl ester. The undecylenyl ester was dissolved in $CH_2Cl_2$, $HSiCl_3$ (9.0 grams) and 2 drops of Pt/DVDMS catalyst were added and resulting mixture was stirred at 40° C. overnight to give the desired material.

Preparative Example 6

Preparation of Hexafluoro-Iso-Propyl-11-(Dimethylchlorosilyl)Undecanoate

A sample of the undecylenyl ester made as described in Preparative Example 7 above was distilled to by 84° C. at about 1 mm Hg. A sample of the undecylenyl ester (20.0 grams) was mixed with $Me_2SiHCl$ (6.0 grams) in toluene, and 2 drops Pt/DVDMS catalyst, heated to 70° C. overnight. The product was distilled to a main fraction by 119° C. at 1 mmHg.

Preparative Example 7

Preparation of Disulfide N-Undecanoyl Perfluoro-Tert-Butyl Ester

DTUA (0.25 gram) is converted to the diacid chloride by reaction with thionyl chloride as described in Preparative Example 1. To this material is added dry THF (2.0 grams) and a mixture of perfluoro-iso-butanol (0.15 gram), ethyl diisopropyl amine (0.08 gram) and THF (0.81 gram). The mixture is stirred overnight.

Example 1

A Gold Film was coated with the disulfide prepared in Preparative Example 1 by dipping the gold film in a solution of the disulfide prepared in Preparative Example 1 (250 micromolar in methyl ethyl ketone) for 1 hour. This coated Gold Film was tested for half life at pH 10 using the test method described above. The result is shown in Table 1. The coated Gold Film was tested for cy5-IgG capture by fluorescence using the test methods described above. The results are summarized in Table 2.

Example 2

A Gold Film was coated with the disulfide prepared in Preparative Example 2 by dipping the gold film in a solution of the disulfide prepared in Preparative Example 2 (250 micromolar in methyl ethyl ketone) for 1 hour. This coated Gold Film was tested for half life at pH 10 using the test method described above. The result is shown in Table 1. The coated Gold Film was tested for cy5-IgG capture by fluorescence using the test methods described above. The results are summarized in Table 2.

Comparative Example C1

A Gold Film was coated with the disulfide prepared in Preparative Example 3 by dipping the gold film in a solution of the disulfide prepared in Preparative Example 3 (250 micromolar in methyl ethyl ketone) for 1 hour. This coated Gold Film was tested for half life at pH 10, using the test method described above. The result is shown in Table 1. The coated Gold Film was tested for cy5-IgG capture by fluorescence using the test methods described above. The results are summarized in Table 2.

Comparative Example C2

A Gold Film was coated with the disulfide prepared in Preparative Example 4 by dipping the gold film in a solution of the disulfide prepared in Preparative Example 4 (250 micromolar in methyl ethyl ketone) for 1 hour. This coated Gold Film was tested for half life at pH 10 using the test method described above. The result is shown in Table 1. The coated Gold Film was tested for cy5-IgG capture by fluorescence using the test methods described above. The results are summarized in Table 2.

TABLE 1

| Example | Half Life at pH 10 (hours) |
|---|---|
| 1 | 78 |
| 2 | 38 |
| C1 | 3.75 |
| C2 | 19.25 |

TABLE 2

| Concentration (microgram/mL) | Fluorescence Example 1 | Fluorescence Example 2 | Fluorescence Example C1 | Fluorescence Example C2 |
|---|---|---|---|---|
| 0 | 160 | 151 | 115 | 132 |
| 1.3 | 458 | 590 | 179 | 235 |
| 5 | 1986 | 2817 | 585 | 850 |
| 13 | 3588 | 6054 | 1497 | 3361 |
| 25 | 4867 | 9750 | 4035 | 4317 |
| 50 | 8404 | 15435 | 10198 | 7810 |
| 130 | 13022 | 27553 | 18645 | 12236 |

We claim:
1. An article comprising a substrate comprising:
(a) an attached tethering group of Formula IV

$$-U-Y-(CO)-OCR^1(R^2)_2 \qquad (IV)$$

that contains a fluoroalkoxycarbonyl group; and
(b) an attached immobilization group of Formula V $$-U-Y-(CO)-NR^4-T \qquad (V)$$

wherein
U is equal to the reaction product of a substrate-reactive functional group X and a complementary group G on a surface of the substrate, wherein said substrate-reactive functional group X is linked to the Y on the compound of Formula (IV) and Formula (V) before the reaction and where X is selected from a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, disulfide, alkyl disulfide, benzotriazolyl, phosphono, phosphoroamido, or phosphato, wherein
group G is a hydroxy, mercapto, primary aromatic amino group, secondary aromatic amino group, or secondary aliphatic amino group when X is carboxy;
group G is a hydroxy, mercapto, primary aromatic amino group, secondary aromatic amino group, or secondary aliphatic amino group when X is halocarbonyl;
group G is a hydroxy, mercapto, primary aromatic amino group, secondary aromatic amino group, or secondary aliphatic amino group when X is halocarbonyloxy;
group G is an azido when X is cyano;
group G is a isocyanato or carboxy when X is hydroxy;
group G is a isocyanato, halocarbonyl, halocarbonyloxy, or ethylenically unsaturated group when X is mercapto;
group G is a hydroxy, mercapto, primary aromatic amino group, secondary aromatic amino group, secondary aliphatic amino group, or carboxylic acid group when X is isocyanato;
group G is a silanol group when X is halosilyl;
group G is a silanol group or metals having hydroxide groups on its surface when X is alkoxysilyl;
group G is a silanol group or metals having hydroxide groups on its surface when X is acyloxysilyl;
group G is a carbon-carbon triple bond, nitrile group, strained olefinic group when X is azido;
group G is a mercapto or carboxylic acid group when X is aziridinyl;
group G is a tertiary amino group when X is haloalkyl;
group G is a haloalkyl when X is tertiary amino;
group G is a metal when X is disulfide;
group G is a metal when X alkyl disulfide;

group G is a metal or metal oxide when X is benzotriazolyl;
group G is metal or metal oxide when X is phosphono;
group G is metal or metal oxide when X is phosphoroamido;
group G is metal or metal oxide when X is phosphate;
Y is a divalent group comprising an alkylene, heteroalkylene, arylene, or combination thereof and optionally further comprising an carbonyl, carbonyloxy, carbonylimino, oxy, —$NR^3$—, or combination thereof;
$R^1$ is selected from hydrogen, fluoro, alkyl, or lower fluoroalkyl;
$R^2$ is a lower fluoroalkyl;
$R^3$ is hydrogen, alkyl, aryl, or aralkyl;
T is equal to the remainder of a primary or secondary biological amino-containing material of formula T-$NHR^4$ absent the amino group —$NHR^4$ wherein the biological amino-containing material is selected from the group consisting of an amino acid, peptide, DNA, RNA, protein, enzyme, organelle, immunoglobulin, and fragments of immunoglobulin; and $R^4$ is selected from hydrogen, alkyl, or a portion of a ring structure connected to group T.

2. The article of claim 1, wherein T is further associated with a second biological material.

3. The article of claim 1, wherein Y is an alkylene or Y comprises a first alkylene connected to at least one other group selected from a heteroalkylene, arylene, second alkylene, carbonyl, carbonyloxy, carbonylimino, oxy, thio, —$NR^3$—, or combination thereof.

4. The article of claim 1, wherein Y is a heteroalkylene or Y comprises a first heteroalkylene connected to at least one other group selected from an alkylene, arylene, second heteroalkylene, carbonyl, carbonyloxy, carbonylimino, oxy, thio, —$NR^3$—,or combination thereof.

5. The article of claim 1, wherein Y is an arylene or Y comprises a first arylene connected to at least one other group selected from an alkylene, heteroalkylene, second arylene, carbonyl, carbonyloxy, carbonylimino, oxy, thio, —$NR^3$—, or combination thereof.

* * * * *